United States Patent [19]

Siepmann et al.

[11] Patent Number: 5,324,666

[45] Date of Patent: Jun. 28, 1994

[54] PROCESS FOR DETERMINING OXIDIZABLE SUBSTANCES CONTAINED IN AN AQUEOUS SAMPLE LIQUID

[76] Inventors: Friedrich W. Siepmann, Oberdorf 34, D-6114 Gross-Umstadt; Michael Teutscher, Neue Str. 7, D-6107 Reinheim/Überau, both of Fed. Rep. of Germany

[21] Appl. No.: 656,042

[22] PCT Filed: Apr. 8, 1989

[86] PCT No.: PCT/EP89/00381

§ 371 Date: Apr. 12, 1991

§ 102(e) Date: Apr. 12, 1991

[87] PCT Pub. No.: WO90/01696

PCT Pub. Date: Feb. 22, 1990

[30] Foreign Application Priority Data

Aug. 13, 1988 [DE] Fed. Rep. of Germany ........ 3827578

[51] Int. Cl.$^5$ ............................................. G01N 33/18
[52] U.S. Cl. ..................................... 436/62; 436/146; 422/79; 210/746; 210/760
[58] Field of Search ............... 422/79; 436/621, 146.1, 436/150, 904; 210/760, 746

[56] References Cited

U.S. PATENT DOCUMENTS

| | | | |
|---|---|---|---|
| 2,055,808 | 9/1936 | Wait | 210/760 |
| 3,276,994 | 10/1966 | Andrews | 210/760 |
| 3,674,216 | 7/1992 | Blair | 210/760 |
| 3,684,702 | 8/1972 | Hartmann | 422/79 |
| 3,731,522 | 5/1973 | Mikesell | 422/79 |
| 3,732,163 | 5/1973 | Lapidot | 210/760 |
| 3,772,188 | 11/1973 | Edwards | 210/760 |
| 4,053,399 | 10/1977 | Donnelly et al. | 210/760 |
| 4,564,453 | 1/1986 | Coplot et al. | 436/62 |
| 4,632,766 | 12/1986 | Firnhaber et al. | 210/760 |
| 5,017,496 | 5/1991 | Klapwijk et al. | 436/62 |

Primary Examiner—Robert J. Warden
Assistant Examiner—Hien Tran
Attorney, Agent, or Firm—Burns, Doane, Swecker & Mathis

[57] ABSTRACT

To analyze the oxidizable substances, for example the chemical oxygen demand (COD), contained in an aqueous sample liquid, for example sewage water, the aqueous sample liquid is diluted with dilution water and fed into a reaction container where it is mixed with ozone from an ozone generating device. After passing through a second reaction container, for example a tubular reactor, the sample liquid reaches an ozonometer appliance. Ozone being added continuously, the ratio of sample liquid to dilution water of the mixture is regulated in such a manner that the residual ozone content measured by the ozonometer appliance remains constant at a predetermined level. The ratio of sample liquid to dilution water of the mixture required to maintain the reading on the ozonometer at the predetermined level is used to determine oxidizable substances contained in the water, in particular COD.

12 Claims, 3 Drawing Sheets

PROCESS FOR DETERMINING OXIDIZABLE SUBSTANCES CONTAINED IN AN AQUEOUS SAMPLE LIQUID

The invention concerns a process for the determination of oxidizable substances contained in water, in particular the chemical oxygen demand (COD) or the organic carbon content (TOC—total organic carbon) of an aqueous sample liquid by the oxidation of organic substances dissolved therein, wherein the sample liquid is diluted in a controlled manner with dilution water.

Processes for the determination of aqueous sample liquids, in particular sewage water, are known. Primarily in the monitoring of sewage and in their discharge into waters and at the inlet and outlet of sewage treatment plants, the determination of the COD values has become increasingly important.

In the known wet chemical processes oxidation of the organic substances dissolved in the sample liquid takes place by reaction with oxidizing agents added. These oxidizing agents and the reaction products generated, are, however, overwhelmingly toxic or at least harmful to the environment, so that their elimination is difficult. In addition, these processes cannot be carried out continuously.

In a known process for the determination of the quantity of organic carbon in a sample liquid (DE-A-24 58 143) a continuous mode of operation is possible. But this process, wherein the quantity of gaseous oxidation products is carried out, is very costly, both relative to the process and the necessary apparatus.

In another known process (DE-A-23 62 773) for the determination of organically bound carbon in water by the oxidation of organic substances, again the carbon dioxide formed by the oxidation is determined. Oxygen or air is used as the oxidizing agent. Under ultraviolet irradiation photochemical oxidation of organic substances takes place, in which a platinum catalyst is used to destroy the ozone generated by the irradiation of oxygen before it is able to contribute to the oxidation. This process does not operate continuously and is therefore not suitable for process control or automatic surveillance. Furthermore, the process is relatively expensive.

In a known process of the aforementioned generic type, electrochemical oxidation of organic substances is effected in a potentiometric measuring layout. In the oxidation of dissolved organic substances at an electrode, electrons are released. Between this electrode and a counter electrode a current flows through a measuring solution, consisting of the sample liquids, diluting water and an electrolyte. This current flow represents at a constant electrode potential a measure of the quantity of the organic substances oxidized. The ability of the electrodes to operate is detrimentally affected if the chemicals contained in the sample liquid form deposits. It is therefore necessary to regenerate the electrode from time to time. For this, the measuring process must be interrupted and a regenerating electrolyte introduced. No uninterrupted, continuous mode of operation is thus possible. In order to determine the necessity or effectiveness of a regenerating process, it is necessary to introduce a standardized calibrating liquid. The efficiency and thus the measuring accuracy of the known process also depends on how strongly the dissolved organic substances tend to be electrochemically oxidized. For this a high electric potential must be maintained between the electrodes, which in turn favors the formation of deposits.

It is the object of the present invention to create a process for the determination of the oxidizable content of water, in particular the chemical oxygen demand (COD) or the total organic carbon (TOC), that may be carried out without the use of dangerous chemical substances and without the difficulties encountered in electrochemical oxidation, rapidly and with an adequately high accuracy, using a moderate array of measuring instruments.

In a continuous process this object is attained according to the invention by that ozone is introduced into the sample liquid for oxidation, that following mixing and oxidation the residual ozone content or the consumption of ozone is determined and that the addition of ozone and/or the sample liquid/dilution water mixing ratio is controlled so that a predetermined constant residual ozone content or ozone consumption is established. The ozone may be added to the dilute sample liquid or to the dilution water.

The use of ozone as the oxidizing agent has the particular advantage that ozone is a very strongly reacting oxidizer, so that any organic substance in contact with is oxidized very rapidly. The time required for the process is essentially determined merely by that the sample liquid must be adequately mixed, so that all of the organic substances contained in it enter into contact with the ozone.

In the process according to the invention the mixing ratio of the sample liquid and the dilution water and optionally the ozone addition must be controlled in a manner such that a high accuracy of the process is obtained. The accuracy depends of the probability of contact between the ozone and the substances to be oxidized and is determined by the mixing ratio.

The measuring process is particularly stable, because it is regulated at a constant residual ozone content or ozone consumption. Since a high concentration of dissolved organic substances would lead to a long reaction time until an informative residual ozone content is obtained, it is a particular advantage of the process according to the invention, that by means of dilution a significantly more rapid reaction of the organic substances with the ozone and thus shorter measuring times are obtained.

Preferably, the enrichment of the dilution water with ozone and the oxidation of the substances contained in the water with the ozone-enriched dilution water take place in two separate reaction spaces and the ozone is measured with two ozone measuring devices, one at the outlet of the ozone enrichment vessel and the other at the outlet of the reaction vessel. By means of such a measuring layout any reduced ozone enrichment by changes in the dilution water, or other effects may be detected and equalized.

If requirements relative to the assurance and accuracy of the analysis are less stringent, this separation of the enrichment and reaction vessels may not be necessary.

In such cases the ozone measurements may be carried out in a simplified manner by measuring the redox potential.

The determination of the redox potential to determine the ozone content of an aqueous liquid is known and represents a low cost and highly reliable measuring method within a limited measuring range of about 400 and 800 mV.

These redox potentials correspond to approximately 0.05 to 0.03 mg ozone per liter in tap water. By the high dilution, measured values similar to those in tap water are obtained. In industrial application of the inventive concept, the ozone introduced should be reduced following the oxidation of the substances contained in the water and the parallel degassing to the aforementioned residual ozone content. Consequently, any "short circuit flow" of ozone from the ozone inlet to the point of measurement must be safely prevented by a proper equipment layout. The "background noise" generated in this manner limits the measuring range of the redox potential measurement to about 400 mV in the downward direction. The upper measuring range is limited by that in tap water without oxidizable substances upon gassing with ozone, a redox potential between 800 and 1000 mV, 900 mV on the average, is obtained. These two limits also indicate how the sensitivity of the instrument may be adjusted. The higher the residual ozone value to be set or obtained, the more similar the outlet concentration of the reaction vessel will be to that of the dilution water and the sensitivity of the process will be higher.

According to a variant of the process of the invention the mixing ratio of the sample liquid to the dilution water is controlled at a constant ozone addition rate so that a constant residual ozone content is obtained and said mixing ratio is then used for the determination of the content of oxidizable substances. This mixing ratio determined readily and with high accuracy; it is subject to slight interferences only, as the residual content is always adjusted to a constant value and therefore stable and well reproducible conditions are present.

According to another variant of the process of the invention, the ozone addition is metered at a constant sample liquid/dilution water ratio so that a constant residual ozone content is established and this ozone addition is used for the determination of oxidizable substances in the water. The rate of ozone addition may also be regulated with an adequate accuracy, for example by adjusting the voltage applied to the ozone generator.

A further variant of the invention concerns a discontinuously operating process for the determination of the content of oxidizable substances in an aqueous sample solution by the oxidation of the organic materials dissolved therein, wherein the sample liquid is diluted at a measured rate with dilution water prior to oxidation and the determination of the oxidizable content in the water is carried out in discrete individual measurements. This process of the invention is characterized in that the period of time to obtain the predetermined residual content is determined and represents a measure of the oxidizable substance content.

This process requires a particularly low apparatus investment and is simple to carry out. A predetermined quantity of the diluted sample liquid is mixed with an also predetermined quantity of ozone under constant mixing conditions, with the residual ozone content or ozone consumption being determined continuously. The period of time required to attain a predetermined residual ozone content serves as a measure of the oxidizable content in the water, in particular the chemical oxygen demand (COD) or the organic carbon content (TOC—total organic carbon).

The higher the concentration of dissolved organic substances, the longer the reaction time to obtain a predetermined residual ozone content. This is a function of the ozone input required and the need to establish contact with the organic substances.

In any case, for the measurement of the oxidizable substances by the addition of ozone and the measurement of the residual ozone, an extensive decomposition of said substances is desired, for example to a "technical decomposition limit" of a residual content of 10%, as the conditions are then more stable.

In a discontinuously operating variant of the inventive concept the sample liquid is metered prior to oxidation, diluted with dilution water and continuously mixed with a metered quantity of ozone per unit time, and the period of time to the attainment of a predetermined residual ozone value measured.

According to the invention, the following process variants are possible:

a) controlling the mixing pumps at a constant residual ozone content;

b) regulating the addition of ozone with constant dilution at a constant residual ozone content;

c) measuring the period of time to the oxidation of the substances contained in the water and detection of the residual ozone.

Each of these variants has its own economical range of application. Thus, with variant a) highly accurate measured values may be obtained within a wide measuring range limited only by the ratio of the mixing pumps. By controlling the pumps, always only a slight, constant concentration of oxidizable substances is introduced into the reaction vessel. With good mixing and an adequate retention time in the reaction vessel of about 5 min, at a volume flow rate of 500 ml/min and a residual ozone content of 80% of the quantity of ozone introduced the desired slight concentration of oxidizable substances (depending on the sensitivity setting) in the reaction vessel may be assured by an ozone load of preferably less than 0.5. This assures a constant retention time of the reagents in the reaction vessel independently of the initial concentration of the liquid to be examined. The dilution prevents excessive foaming and thus insures during the introduction of the ozone into a gaseous mixture a trouble free operation.

Variant b) is technically simpler to carry out than Variant a). The measuring range should vary within narrower limits, such as those in COD measurements at the outlet of a sewage treatment plant, as with a constant retention time in the reaction vessel, different COD concentrations are to be oxidized to the same terminal degree of decomposition. This disadvantage may be in part compensated mathematically and/or equalized by a higher certainty of the retention time in the reaction vessel.

Variant c) may be effected with a technically much simpler apparatus in a discontinuous operation.

Advantages embodiments of the process according to the invention are the object of dependent claims, together with devices to carry out the processes.

BRIEF DESCRIPTION OF THE DRAWINGS

The processes according to the invention and equipment to carry them out are explained in more detail below with reference to the drawing, in which.

DESCRIPTION OF THE PREFERRED EMBODIMENTS

Figure 1:
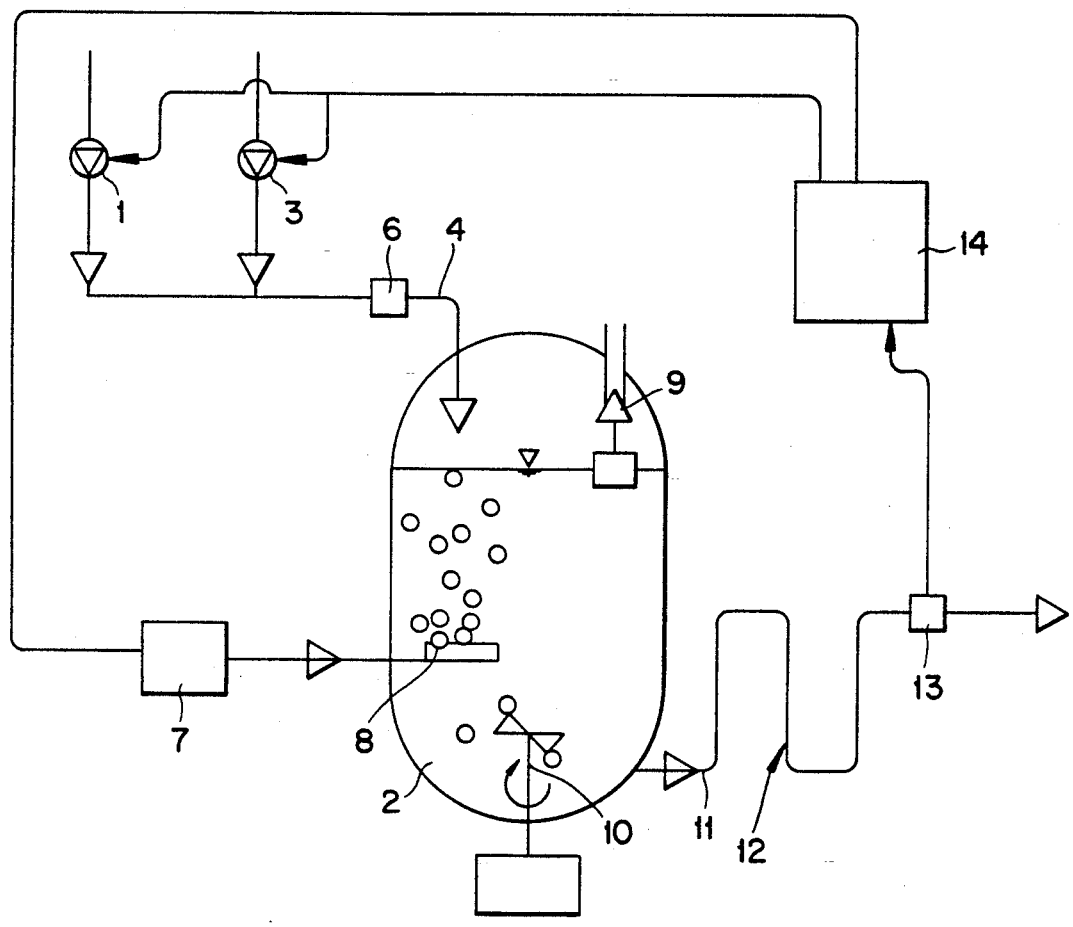
FIG. 1 shows in a schematic view an apparatus to carry out the continuous process according to the invention, FIG. 2 again schematically an apparatus to carry out a discontinuous process of the invention, FIG. 3 a diagram in which the redox potential is plotted over the ozone content, FIG. 4 a schematic view of another apparatus to carry out the process according to the invention, and FIG. 5 a diagram, in which the ozone load is plotted over the ozone consumption.

In the apparatus shown in FIG. 1 for COD determination the sample liquid, for example sewage, is introduced by means of a metering pump 1 into a closed reaction vessel 2. Simultaneously, dilution water is added by means of a metering pump 3. In the feed line 4 of the reaction vessel 2 a redox potential measuring cell 6 is located to measure the redox potential of the mixture introduced, said cell 6 representing the ozone measuring device.

An ozone generator 7, which supplies through a bubbling device 8 a measurable volume flow of ozone to the reaction vessel, forms the oxidation apparatus.

A degassing valve 9 makes possible the exhaust of the gas volume that has not reacted or dissolved.

A mixing apparatus 10 shown in FIG. 1 schematically only as an agitator, serves to mix together the content of the reaction vessel 2 and to comminute potentially present solid particles entrained by the sewage.

The sample liquid passes from the reaction vessel 2 into a vessel outlet line 11, in which a tubular reactor 12, for example in the form of a pipe coil, is located. A redox potential measuring cell 13 is located at the end of the tubular reactor as the ozone measuring instrument. The measuring cell 13 measures the residual ozone content attained following the reaction period, which is determined by the mixing process in the reaction vessel 2 and the plug flow through the tubular reactor 12. The tubular reactor 12 is to prevent a short-circuit flow of ozone from the bubbling device 8 directly to the redox potential measuring cell 13, as this would falsify the results of the measurement. It assures a minimum reaction time.

The measured result of the redox measuring cell 13 is passed to a control device 14, which regulates the metering pumps 1, 3 and/or the ozone generator 7.

The process is regulated for example by that the ozone input is maintained constant by the ozone generator 7 and the mixing ratio of the sample liquid/dilution water controlled so that in the redox potential measuring cell 13, aside from control fluctuations, a predetermined constant redox potential is established. This predetermined constant redox potential is chosen to be within a range of 300 to 800 mV, preferably about 700 mV.

Alternatively, the metering pumps 1 and 3 may be set for a constant dilution ratio. The regulating device 14 then controls the ozone input through the ozone generator 7, so that again the constant redox potential is established in the redox potential measuring cell 13.

As the temperature also affects the reaction, the temperature of the dilute sample liquid is conveniently determined and maintained constant at 25°.

The carbonate hardness of the dilution water added of the dilute sample liquid has an effect on the reaction and should thus be measured and maintained constant. It is particularly convenient to establish a carbonate hardness of about 0 by softening the dilution water.

Figure 2:
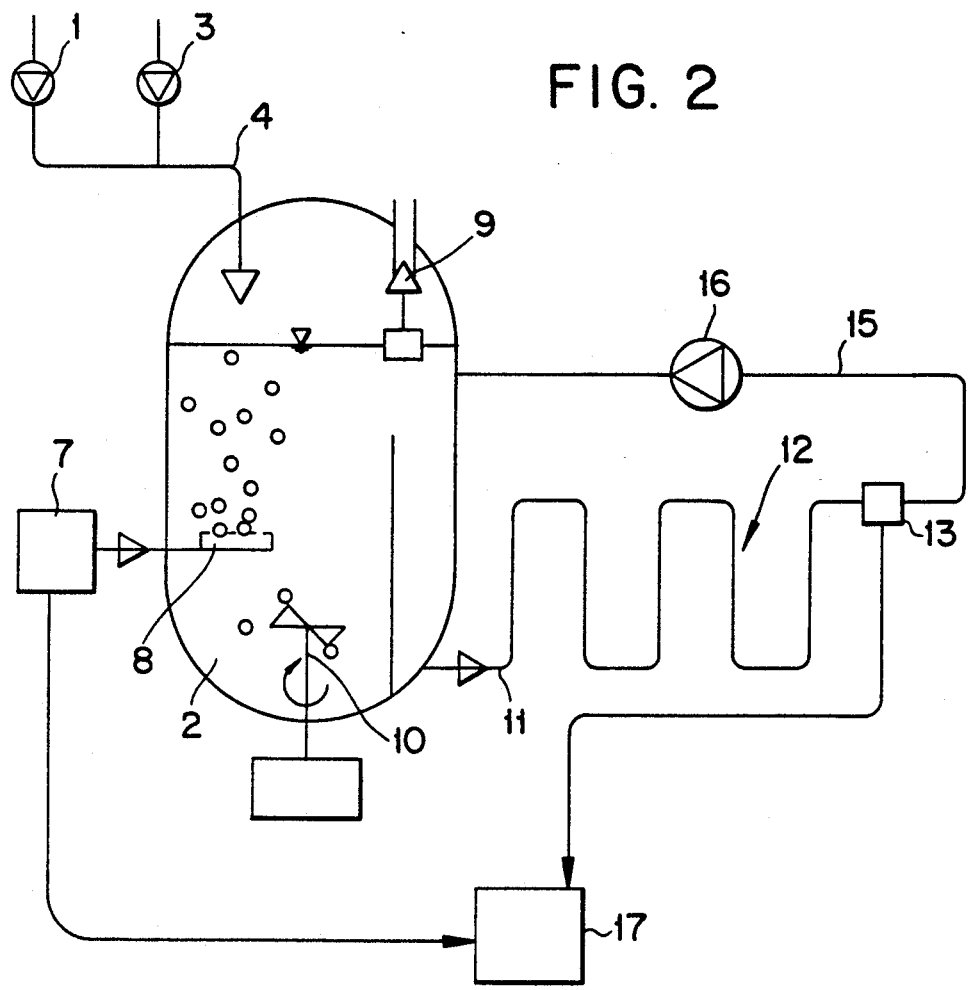

Another apparatus to carry out a modified process is seen in FIG. 2. The configuration of the reaction vessel and other parts is similar to that of FIG. 1 and are therefore identified by the same symbols. The apparatus shown in FIG. 2 differs from the apparatus of FIG. 1 essentially by that the reaction vessel is filled not continuously but by lots. The sample liquid is recycled through the tubular reactor 12 and the redox potential measuring cell 13 and a circulating line 15, by means of a circulating pump 16, to the reaction vessel 2. After the metering pumps 1 and 3 had introduced a predetermined mixture of the sample liquid and the dilution water in measured quantities into reaction vessel 2 and the ozone generator 7 has fed in a predetermined volume of ozone, the mixture is circulated by the circulating pump 16 until the predetermined redox potential is established in the redox potential measuring cell 13, said potential having chosen as a example at 700 mV. In an evaluating circuit 17, connected with the ozone generator and redox potential measuring cell 13, the period of time between the introduction of the ozone and the attainment of the predetermined redox potential value is determined and is used as a measure of COD.

Figure 3:
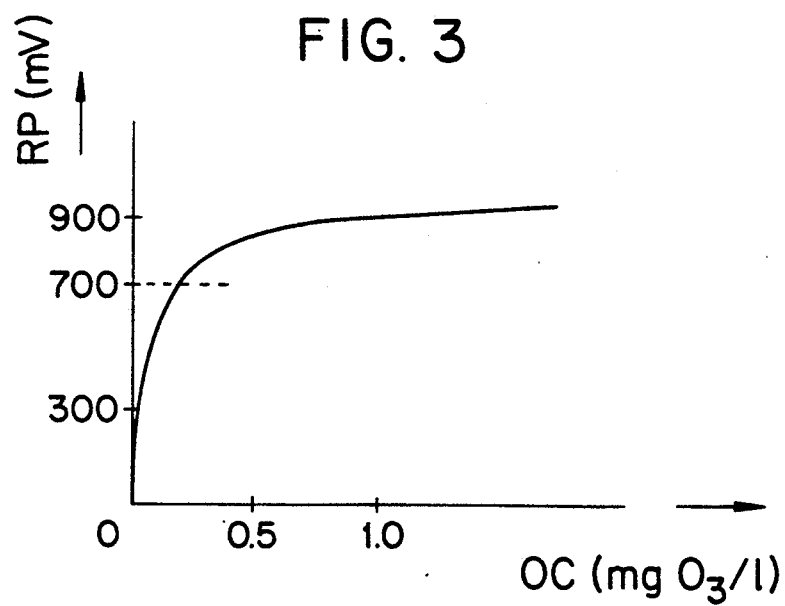

FIG. 3 shows the variation of the redox potential RP over the ozone content OC.

Figure 4:
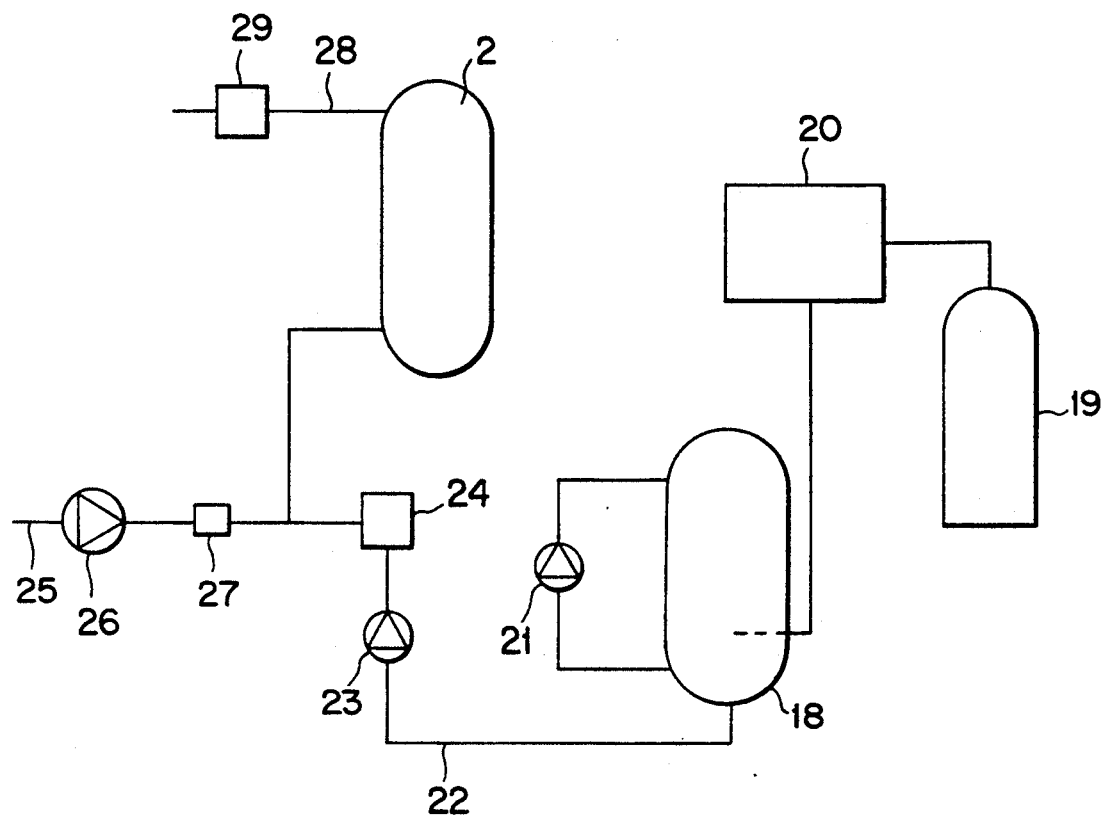

In the apparatus shown in a simplified manner in FIG. 4 for the embodiment of the process, the dilution water is enriched with ozone in an enrichment reaction vessel 18 prior to the mixing with the sewage. For the purpose, an ozone generator 20 connected with a source of oxygen 19 is connected with the reaction vessel 18.

A circulating pump 21 connected by means of a feed line and a return line with the reaction vessel 18, provides an intensive mixing of the dilution water with the ozone introduced. A line 22 leads from the reaction vessel 18 through a dilution water pump 23 and an ozone measuring device in the form of an ozone measuring probe 24 into a reaction vessel 2'.

A line 25 also leads into said reaction vessel 2', whereby sewage is introduced as the sample liquid through a sewage pump 26 and a magnetic valve 27. The mixing of the sewage introduced in measures quantities with the dilution water enriched in ozone and also introduced in metered quantities, is effected in this manner.

The oxidation of the substances contained in the sewage water takes place in the reaction vessel 2'. In the outlet line 28 of the reaction vessel 2' another ozone measuring device 29 is located in the form of an ozone measuring probe.

By controlling the pumps 23 and 26 and/or the ozone generator 20, the mixing ratio of the sewage water to the dilution water and/or the addition of the ozone are regulated in a manner such that on the ozone measuring device 29 a predetermined constant ozone content or—by means of difference measurements on the ozone measuring devices 24 and 29—a predetermined constant ozone consumption, is established. The mixing ratio established by the pumps 23 and 26 or the ozone addition set on the ozone generator 20 represent a measure of the oxidizable substances contained in the water of the sewage introduced through the line 25 or another sample liquid.

In the description of the examples of embodiment only a COD determination was discussed in a simplified fashion. However, the examples are valid generally for the determination of oxidizable substances contained in water, for example TOC.

In the process described, the control of the mixing ratio of the sample liquid and the dilution water, optionally in combination with the regulation of the ozone addition, is particularly important. Thus, the accuracy of the process depends to a great extent on the contact time and the probability of contact between the ozone and the substances to be oxidized. The contact time is determined by the dimensioning of the reaction vessel. The contact probability is defined by the ratio of the ozone dissolved in the dilution water and the substances contained in the sewage water. This relationship is defined here as the ozone load, as follows:

$$\text{Ozone charge} = \frac{COD \text{ load(mg/min)}}{\text{ozone load(mg/min)}}$$

Figure 5:
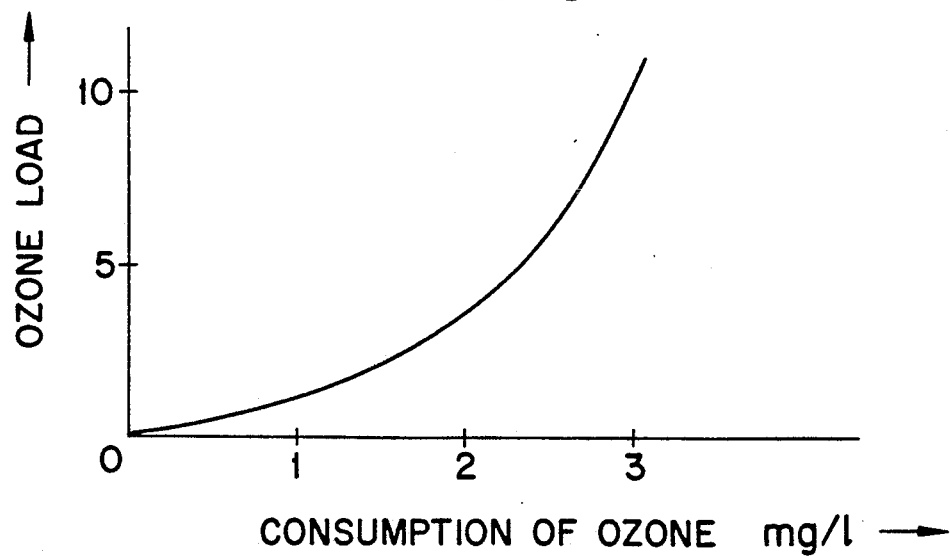

FIG. 5 clearly shows that the setting of a residual ozone content or an ozone consumption determines the reaction conditions for the case of a constant reaction vessel, and thus the sensitivity and the measuring range of the measuring process.

In order to obtain a high accuracy, the setting of the "ozone load" at a working point within a range of less than 0.5 is recommended.

The accuracy of the process is thus limited only by the control range of the pumps. By increasing the ozone input the measuring range may be extended upwards. Measurements above this range is possible, but with reduced accuracy.

We claim:

1. A process for the determination of oxidizable substances contained in a water sample, comprising steps of:
   (a) obtaining a sample liquid containing oxidizable substances;
   (b) diluting the sample liquid with dilution water;
   (c) adding ozone to one of the sample liquid or the dilution water prior to addition of dilution water to the sample liquid in step (b);
   (d) mixing the ozone and diluted sample liquid, thereby effecting oxidation of at least a portion of the oxidizable substances in said sample liquid;
   (e) measuring one of a residual, unreacted ozone content or a consumption of ozone; and
   (f) regulating the addition of ozone or the mixing ratio of sample liquid to dilution water based on the measured residual, unreacted ozone content or the ozone consumption in step (e) to maintain a constant level of the residual, unreacted ozone content or the consumption of ozone.

2. A process according to claim 1, wherein the sample liquid is diluted with dilution water prior to the addition of ozone.

3. A process according to claim 1, wherein the step of adding ozone includes adding ozone to the dilution water and subsequently mixing the thereby ozone enriched dilution water with the sample liquid.

4. A process according to claim 3, wherein ozone addition to dilution water in step (c) and oxidation in step (d) are carried out in separate reaction zones, and wherein ozone measurement is effected at an outlet of each of said reaction zones.

5. A process according to claim 1, wherein the residual, unreacted ozone content is determined by measuring a redox potential of the diluted sample liquid before or after adding ozone.

6. A process according to claim 5, wherein the redox potential is predetermined within a range of from 300 to 800 mV.

7. A process according to claim 1, wherein the ozone consumption is determined by direct ozone measurements of the diluted sample liquid made both prior to the addition of ozone and after the oxidation.

8. A process according to claim 1, wherein the oxidizable substances are measurable as chemical oxygen demand, and wherein said process provides for maintaining in step (f) a ratio of chemical oxygen demand to added ozone of no more than 0.5.

9. A process according to claim 1, wherein the determination of residual, unreacted ozone content is carried out within a range of from 0.05 to 0.3 mg ozone per liter of tap water.

10. A process according to claim 1, wherein the rate of ozone addition is constant, and the mixing ratio of sample liquid to dilution water is controlled to maintain a constant residual ozone content or ozone consumption, and wherein said mixing ratio is used to determine the amount of oxidizable substances contained in the sample liquid.

11. A process according to claim 1, wherein the mixing ratio of sample liquid to dilution water is constant, and wherein the ozone addition is metered to provide a constant residual, unreacted ozone content or ozone consumption, and wherein the amount of ozone addition is used to determine the amount of oxidizable substances contained in the sample liquid.

12. A process for the determination of oxidizable substances contained in an aqueous sample liquid, comprising the steps of:
   (a) diluting a sample liquid containing oxidizable substances with dilution water in a controlled manner;
   (b) introducing ozone in the sample liquid for oxidation of the oxidizable substances in measured quantities;
   (c) mixing the ozone introduced in step (b) and thereby effecting oxidation of the oxidizable substances; and
   (d) measuring a residual ozone content in the sample liquid, wherein the period of time for obtaining a predetermined constant residual ozone content is determined and provides a measure of the oxidizable substances contained in the sample liquid.

* * * * *